United States Patent
Hildebrand et al.

(10) Patent No.: US 8,447,086 B2
(45) Date of Patent: May 21, 2013

(54) LENS CAPSULE SIZE ESTIMATION

(75) Inventors: Daniel Hildebrand, San Francisco, CA (US); David John Smith, Highland, CA (US); Claudio Argento, Los Gatos, CA (US)

(73) Assignee: PowerVision, Inc., Belmont, CA (US)

( * ) Notice: Subject to any disclaimer, the term of this patent is extended or adjusted under 35 U.S.C. 154(b) by 449 days.

(21) Appl. No.: 12/872,314

(22) Filed: Aug. 31, 2010

(65) Prior Publication Data
US 2011/0052020 A1    Mar. 3, 2011

Related U.S. Application Data

(60) Provisional application No. 61/238,606, filed on Aug. 31, 2009.

(51) Int. Cl.
*G06K 9/62* (2006.01)
(52) U.S. Cl.
USPC ............ 382/128; 359/290; 359/291; 359/292
(58) Field of Classification Search
USPC .......... 382/128; 359/290–292; 351/FOR. 109
See application file for complete search history.

(56) References Cited

U.S. PATENT DOCUMENTS

| | | | |
|---|---|---|---|
| 4,111,995 A | 9/1978 | Nelson | |
| 4,253,199 A | 3/1981 | Banko | |
| 4,254,509 A | 3/1981 | Tennant | |
| 4,304,895 A | 12/1981 | Loshaek | |
| 4,373,218 A | 2/1983 | Schachar | |
| 4,409,691 A | 10/1983 | Levy | |
| 4,423,809 A | 1/1984 | Mazzocco | |
| 4,435,856 A | 3/1984 | L'Esperance | |
| 4,466,705 A | 8/1984 | Michelson | |
| 4,490,860 A | 1/1985 | Rainin | |
| 4,494,254 A | 1/1985 | Lopez | |
| 4,512,040 A | 4/1985 | McClure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A | 10/1986 | Woods | |
| 4,620,954 A | 11/1986 | Singer et al. | |
| 4,685,921 A | 8/1987 | Peyman | |
| 4,685,922 A | 8/1987 | Peyman | |
| 4,693,717 A | 9/1987 | Michelson | |
| 4,720,286 A | 1/1988 | Bailey et al. | |
| 4,731,078 A | 3/1988 | Stoy et al. | |

(Continued)

FOREIGN PATENT DOCUMENTS

| | | |
|---|---|---|
| EP | 0898972 A2 | 3/1999 |
| FR | 2784575 | 4/2000 |

(Continued)

OTHER PUBLICATIONS

Langenbucher, A., & Seitz, B. (2004). Computerized calculation scheme for toric intraocular lenses. Acta Ophthalmologica Scandinavica, 82(3), 270-276. doi: http://dx.doi.org/10.1111/j.1600-0420.2004.00264.x.*

(Continued)

*Primary Examiner* — Mark Holcomb
(74) *Attorney, Agent, or Firm* — Shay Glenn LLP

(57) ABSTRACT

Methods of estimating the size of an ocular lens capsule.

6 Claims, 3 Drawing Sheets

U.S. PATENT DOCUMENTS

| | | |
|---|---|---|
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,171,266 A | 12/1992 | Wiley et al. |
| 5,200,430 A | 4/1993 | Federman |
| 5,201,763 A | 4/1993 | Brady et al. |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,843,188 A | 12/1998 | McDonald |
| 5,891,931 A | 4/1999 | Leboeuf et al. |
| 5,928,282 A | 7/1999 | Nigam |
| 5,964,802 A | 10/1999 | Anello et al. |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch |
| 7,070,276 B2 * | 7/2006 | Koretz ........................ 351/206 |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,168 B2 | 7/2007 | Esch et al. |
| 7,247,689 B2 | 7/2007 | Makker et al. |
| 7,261,737 B2 | 8/2007 | Esch et al. |

| Patent/Pub No. | Date | Name |
|---|---|---|
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,416,300 B2 * | 8/2008 | Wei et al. .................. 351/159.75 |
| 7,438,723 B2 | 10/2008 | Esch |
| 7,453,646 B2 | 11/2008 | Lo |
| 7,485,144 B2 | 2/2009 | Esch |
| 7,494,505 B2 | 2/2009 | Kappelhof et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,776,088 B2 | 8/2010 | Shadduck |
| 7,832,864 B2 | 11/2010 | Barrett et al. |
| 7,878,655 B2 * | 2/2011 | Salvati et al. .................. 351/221 |
| 7,971,997 B2 * | 7/2011 | Hiramatsu et al. ............ 351/212 |
| 7,988,290 B2 | 8/2011 | Campbell et al. |
| 7,988,292 B2 | 8/2011 | Neal et al. |
| 7,988,293 B2 | 8/2011 | Raymond et al. |
| 8,162,927 B2 | 4/2012 | Peyman |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0230203 A1 | 11/2004 | Yaguchi |
| 2005/0021139 A1 | 1/2005 | Shadduck |
| 2005/0113911 A1 | 5/2005 | Peyman |
| 2005/0131535 A1 | 6/2005 | Woods |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0158611 A1 * | 7/2006 | Piers et al. .................... 351/177 |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Nun |
| 2007/0299487 A1 | 12/2007 | Shadduck |
| 2008/0004699 A1 | 1/2008 | Nun |
| 2008/0015689 A1 | 1/2008 | Esch et al. |
| 2008/0027537 A1 | 1/2008 | Gerlach et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200982 A1 | 8/2008 | Your |
| 2008/0243247 A1 | 10/2008 | Poley et al. |
| 2008/0269887 A1 | 10/2008 | Cumming |
| 2008/0269987 A1 | 10/2008 | Barron et al. |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0027661 A1 | 1/2009 | Choi et al. |
| 2009/0030425 A1 | 1/2009 | Smiley et al. |
| 2009/0076602 A1 | 3/2009 | Ho et al. |
| 2009/0124773 A1 | 5/2009 | Zhou et al. |
| 2009/0149952 A1 | 6/2009 | Shadduck |
| 2009/0228101 A1 | 9/2009 | Zadno-Azizi |
| 2009/0234449 A1 | 9/2009 | DeJuan, Jr. et al. |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2010/0039709 A1 | 2/2010 | Lo |
| 2010/0063588 A1 | 3/2010 | Park |
| 2010/0094412 A1 | 4/2010 | Wensrich |
| 2010/0131058 A1 | 5/2010 | Shadduck |
| 2010/0179653 A1 | 7/2010 | Argento et al. |
| 2010/0228344 A1 | 9/2010 | Shadduck |
| 2010/0228346 A1 | 9/2010 | Esch |
| 2011/0118834 A1 | 5/2011 | Lo et al. |
| 2011/0153015 A1 | 6/2011 | Simonov et al. |
| 2012/0078363 A1 | 3/2012 | Lu |
| 2012/0078364 A1 | 3/2012 | Stenger |
| 2012/0179249 A1 | 7/2012 | Coleman |
| 2012/0226351 A1 | 9/2012 | Peyman |
| 2012/0245591 A1 | 9/2012 | Matthews |
| 2012/0253459 A1 | 10/2012 | Reich et al. |

FOREIGN PATENT DOCUMENTS

| | | |
|---|---|---|
| JP | 07-044938 | 5/1995 |
| JP | 9294754 | 11/1997 |
| JP | 10-206609 | 8/1998 |
| JP | 11276509 | 10/1999 |
| SU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 2/2004 |
| WO | WO 2004/010895 A2 | 2/2004 |
| WO | WO 2004/046768 A2 | 6/2004 |
| WO | WO 2004/072689 A2 | 8/2004 |
| WO | WO 2005/084588 A1 | 9/2005 |
| WO | WO 2006/004707 A2 | 1/2006 |
| WO | WO2006/011937 A2 | 2/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO 2007/138564 A1 | 12/2007 |
| WO | WO 2009/100322 A2 | 8/2009 |
| WO | WO 2009/154455 A1 | 12/2009 |
| WO | WO2012/006186 A2 | 1/2012 |

OTHER PUBLICATIONS

Qiao et al.; Bio-inspired accommodating fluidic intraocular lens; Optics Letters; vol. 34; No. 20; pp. 3214-3216; Oct. 15, 2009.
Shadduck, John H.; U.S. Appl. No. 13/300,245 entitled "Accommodating Intraocular Lenses and Methods of Use," filed Nov. 18, 2011.
Anvar et al.; U.S. Appl. No. 13/033,474 entitled "Fluid for Accommodating Intraocular Lenses," filed Feb. 23, 2011.
Scholl et al.; U.S. Appl. No. 13/193,487 entitled "Accommodating Intraocular Lenses," filed Jul. 28, 2011.
Smiley et al.; U.S. Appl. No. 13/193,983 entitled "Accommodating Intraocular Lenses," filed Jul. 29, 2011.
Smiley et al.; U.S. Appl. No. 13/194,004 entitled "Accommodating Intraocular Lenses," filed Jul. 29, 2011.
Hildebrand et al.; U.S. Appl. No. 13/180,427 entitled "Intraocular lens delivery devices and methods of use," filed Jul. 11, 2011.
Baughman et al., "Negative poisson's ratios for extreme states fo matter," Science, vol. 288, pp. 2018-2022, Jun. 16, 2000.
Baughman, "Avoiding the shrink," Nature, vol. 425, pp. 667, Oct. 16, 2003.
Conlisk, A. T. et al; Mass Transfer and Flow in Electrically Charged Micro-and Nano-channels; Analytical Chemistry, vol. 74; iss. 9; pp. 2139-2150; 2002.
Dubbelman et al.; The Thickness of the Aging Human Lens Obtained from Corrected Scheimpflug Images; Optometry & Vison Science; vo. 78; iss. 6; pp. 411-416; Jun. 2001.
Gorder, P. F.; Electricity can pump medicine in implanted medical devices; Ohio State Research News; 3 pgs.; May 2, 2002 (printed from internet Aug. 19, 2010).
Gordon, "Applications of shape memory polyurethanes," Proceedings of the First Intl Conf. on Shape Memory and Superelastic Tech., Asilomar Conference Center, Pacific Grove, CA, USA, pp. 115-120, 1994.
Gruber et al.; Exhaustive soxhlet extraction for the complete removal of residual compounds . . . ; Journal of Biomedical Materials Research; vol. 53; No. 5; pp. 445-448; Mar. 2000.
Jeon et al., "Shape memory and nanostructure in poly(norbornyl-POSS) copolymers," Polymer International, vol. 49, pp. 453-457, 2000.
Kim et al., "Polyurethanes having shape memory effects," Polymer, vol. 37, No. 26, pp. 5781-5793, 1996.
Lakes et al., "Dramatically stiffer elastic composite materials due to negative stiffness phase?," Journal of the Mechanics and Physics of Solids, vol. 50, pp. 979-1009, 2002.

Li et al., "Crystallinity and morphology of segmented polyurethanes with different soft-segment length," Journal of Applied Polymer Science, vol. 62, pp. 631-638, 1996.
Liu et al., "Thermomechanical characterization of a tailored series of shape memory polymers," Journal of Applied Medical Polymers, vol. 6, No. 2, 2002.
Mather et al., "Strain recovery in POSS hybrid thermoplastics," Polymer Preprints, vol. 41, No. 1, pp. 528-529, 2000.
Metcalfe et al., "Cold hibernated elastic memory foams for endovascular interventions," Biomaterials, vol. 24, pp. 491-497, 2003.
Rosales et al.; Pentacam Scheimpflug QuantitativeImaging of the Crystalline Lens andIntraocular Lens; J. Refractive Surgery; vol. 25; pp. 421-428; May 2009.
Takahashi et al., "Structure and properties of shape-memory polyurethane block copolymers," Journal of Applied Polymer Science, vol. 60, pp. 1061-1069, 1996.
Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.
Tobushi et al., "Thermomechanical properties of shape memory polymers of polyurethane series and their applications," Journal de Physique IV, Colloque C1, vol. 6, pp. 377-384, 1996.
Vass et al.; Prediction of pseudophakic capsular bag diameter based on biometric variables; J Cataract Refract Surg.; vol. 25; pp. 1376-1381; 1999.
Wang et al., "Deformation of extreme viscoelastic metals and composites," Materials Science and Enginerring A, vol. 370, pp. 41-49, 2004.
Wang et al., "Extreme stiffness systems due to negative stiffness elements," American Journal of Physics, vol. 72, No. 1, pp. 40-50, Jan. 2004.
Wang et al., "Stable extremely-high-damping discrete viscoelastic systems due to native stiffness elements," Applied Physics Letters, vol. 84, No. 22, pp. 4451-4453, May 31, 2004.
Wyant et al; "Basic Wavefront Aberration Theory for Optical Metrology," Applied Optics and Optical Engineering, vol. XI, 1992: pp. 1, 28-39.
Xu et al., "Basic negative poisson's ratio microstructures by soft lithography," Advanced Materials, vol. 11, No. 14, 1999, pp. 1186-1189, 1999.
Shadduck, John H.; U.S. Appl. No. 12/852,733 entitled "Intraocular Lens System and Method for Power Adjustment," filed Aug. 9, 2010.
Esch et al.; U.S. Appl. No. 12/853,892 entitled "Accommodating Intraocular Lens Having Peripherally Actuated Deflectable Surface and Method," filed Aug. 10, 2010.
Lakes et al., "Extreme damping in composite materials with negative-stiffness inclusions," Nature, vol. 410, pp. 565-567, Mar. 29, 2001.
Lakes et al., "Microbuckling instability in elastomeric cellular sollids," J. Materials Science, vol. 28, pp. 4667-4672, 1993.
Lakes, "A broader view of membranes," Nature, vol. 414, pp. 503-504, Nov. 29, 2001.
Lakes, "Extreme damping in compliant composites with a negative-stiffness phase," Philosophical Magazine Letters, vol. 81, No. 2, pp. 95-100, 2001.
Lakes, "Extreme damping in composite materials with a negative stiffness phase," Physical Review Letters, vol. 86, No. 13, pp. 2897-2900, Mar. 26, 2001.
Lakes, "Lateral deformations in extreme matter," Science, vol. 288, pp. 1976, Jun. 2000; 3 pgs.
Lakes, "Negative poisson's ratio materials," Science, vol. 238, pp. 551, Oct. 23, 1987.
Lakes, "No contractile obligations," Nature, vol. 358, pp. 713-714, 1992.
Lendlein et al., "Biodegradable, elastic shape-memory polymers for potential biomedical applications", Science; vol. 296; pp. 1673-1676; May 31, 2002.
Lendlein et al., "Shape-memory polymers," Angew. Chem. Int. Ed.; vol. 41; pp. 2034-2057; 2002.

* cited by examiner

LENS CAPSULE SIZE ESTIMATION

CROSS-REFERENCE TO RELATED APPLICATIONS

This application claims priority under 35 U.S.C §119 to U.S. Provisional Patent Application No. 61/238,606, filed Aug. 31, 2009, which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference herein.

BACKGROUND OF THE INVENTION

An intraocular lens ("IOL") can be used to replace a native lens of the eye when the native lens has been clouded by a cataract, or when the native lens loses part or all of its ability to accommodate. Non-accommodating IOLs have been described, including fixed monofocal IOLs and multifocal IOLs. Accommodating IOLs have also been described, which have accommodative capabilities similar to a native lens.

To replace a native lens with an IOL, the native lens is first removed from the capsular bag (typically by emulsification), leaving the capsular bag in the eye. The IOL is then implanted within the capsular bag. It is generally beneficial to ensure that the IOL to be implanted is appropriately sized based on the size of the patient's capsular bag. It may be even more important to ensure that an accommodating IOL is appropriately sized because, unlike a non-accommodating IOL, an accommodating IOL accommodates in response to changes in shape of the capsular bag. The accommodative response of an accommodating IOL may therefore depend on the appropriateness of the fit between the IOL and the capsular bag. Determining, or estimating, the size of the capsular bag before implanting the IOL is therefore generally beneficial, and may even greatly enhance the accommodative response of an accommodating IOL.

Techniques have been described to estimate the size of a capsular bag, but they have shortcomings which result in a need for improved methods of estimating the capsular bag size. For example, magnetic resonance imaging (MRI) can be used to non-invasively measure the dimensions of the capsular bag. The image resolution is, however, typically about ±0.1 mm or more. Moreover, the MRI slice thickness is generally too thick to get an accurate estimation of the true equatorial diameter of the lens capsule since there are typically only 3-5 images taken across the lens. Attempting to decrease the slice thickness creates a longer scanning time and this creates images with more motion noise as the patient's eye slightly moves over the course of the scan. Additionally, the access to, cost, and analysis of a MRI scan makes this technique prohibitive for IOL applications.

While optical coherence tomography (OCT) could be used to non-invasively measure the anterior lens radius, current clinical OCT devices do not have the capability to image a significant portion of the lens radii due to the iris. OCT measurements are currently made along or parallel to the optical axis of the eye. Therefore, the area of the lens surfaces that can be imaged is limited by the iris. Accurately calculating lens radii is highly dependent on the amount of lens surface (arc length) that can be imaged as well as ensuring axial alignment so that the true lens center is being imaged. As understood, OCT methods, unlike Scheimpflug methods, currently do not rotationally 'scan' the lens which is needed in order to reconstruct the true shape of the lens since asymmetries may be present. Like Scheimpflug imaging, OCT images also require distortion correction due to the different indices of refraction that the light travels through. OCT may a potential method if the issues mentioned above can be addressed.

Invasive methods such as capsular tension rings (see, e.g., Vass, C. et al. Prediction of pseudophakic capsular bag diameter based on biometric variables. J Cataract Refract Surg. 1999; 25:1376-1381, which is incorporated by reference herein) and capsule measurement rings (see, e.g., Tehrani, M. et al. Capsule measuring ring to predict capsular bag diameter and follow its course after foldable intraocular lens implantation, J Cataract Refract Surg. 2003; 29:2127-2134, which is incorporated by reference herein) have been used to estimate capsule size. These methods involve the implantation of a flexible, incomplete (<360°) ring which has an unrestrained diameter greater than the diameter of the capsular bag. When the ring is placed in the capsular bag after lens removal, the ring stretches out the capsule like a low-stiffness spring. By measuring the distance between features on the ring before and after implantation, a measurement of the stretched capsule diameter can be made. Since these methods are invasive and are deforming the capsular bag they can only obtain an equivalent diameter measurement and not a true volumetric measurement of the capsular bag, unlike Scheimpflug imaging (and possibly small-slice thickness MRI and rotationally scanning OCT). Additionally, invasive methods are not ideal as the correct size of the replacement IOL must be available at the time of measurement as opposed to non-invasive methods which allow the surgeon time to acquire the appropriate device or revise the treatment strategy.

SUMMARY OF THE INVENTION

One aspect of the disclosure is a method of estimating the size of an ocular lens capsule. The method includes obtaining patient data of a subject; imaging an anterior surface of an ocular lens and a posterior surface of the ocular lens; estimating a refractive index of the ocular lens; correcting the image of the anterior surface of the ocular lens for distortion to determine a radius of curvature of the anterior surface of the ocular lens; correcting the image of the posterior surface of the ocular lens for distortion to determine a radius of curvature of the posterior surface of the ocular lens; determining a thickness of the ocular lens using the corrected images of the anterior and posterior surfaces; estimating an estimated radius of curvature of the posterior surface of the ocular lens and an estimated lens thickness using the estimated refractive index, the patient data, and the radius of curvature of the anterior surface of the ocular lens; determining a difference between the determined radius of curvature of the posterior surface and the estimated radius of curvature of the posterior surface, and determining a difference between the thickness of the lens and the estimated lens thickness; minimizing at least one of the differences by repeating the estimating step and the determining step with an adjusted estimated refractive index; creating a geometric model of the capsule using the radii of curvature of the anterior surface, the posterior surface, and the lens thickness; and selecting an intraocular lens for implantation based on the computed geometric model.

In some embodiments the method further comprises computing a capsular bag diameter from the geometric model.

In some embodiments estimating the refractive index comprises estimating a refractive index of the ocular lens using the patient data.

In some embodiments the method further comprises fitting end caps into the geometric model to compute the capsular bag diameter.

In some embodiments the method further comprises using an estimated lens elasticity to compute the capsular bag diameter.

In some embodiments imaging an anterior surface of an ocular lens and a posterior surface of the lens comprises imaging the anterior surface of an ocular lens and a posterior surface of the lens with a Scheimpflug imaging system.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The disclosure herein relates generally to methods of estimating the size of a capsular bag in an eye. The methods herein can be used to determine an appropriately-sized IOL to be implanted in a subject following the estimation, but the methods are not limited to this use. As used herein, capsular bag "size" includes, without limitation, any dimension of a capsular bag, a general shape of the bag or portions of the bag, volume, etc.

The estimation methods described herein can be performed on a capsule bag when the capsule is in a subject (in vivo), on an artificial capsular bag which is part of an artificially created eye, or on a native capsule bag which is part of an eye from a subject (such as an animal) which has been removed from the subject. The methods are performed while the lens is still within the capsule, but in some instances some measurements may be made after the lens has been removed from the capsule.

Figure 1:
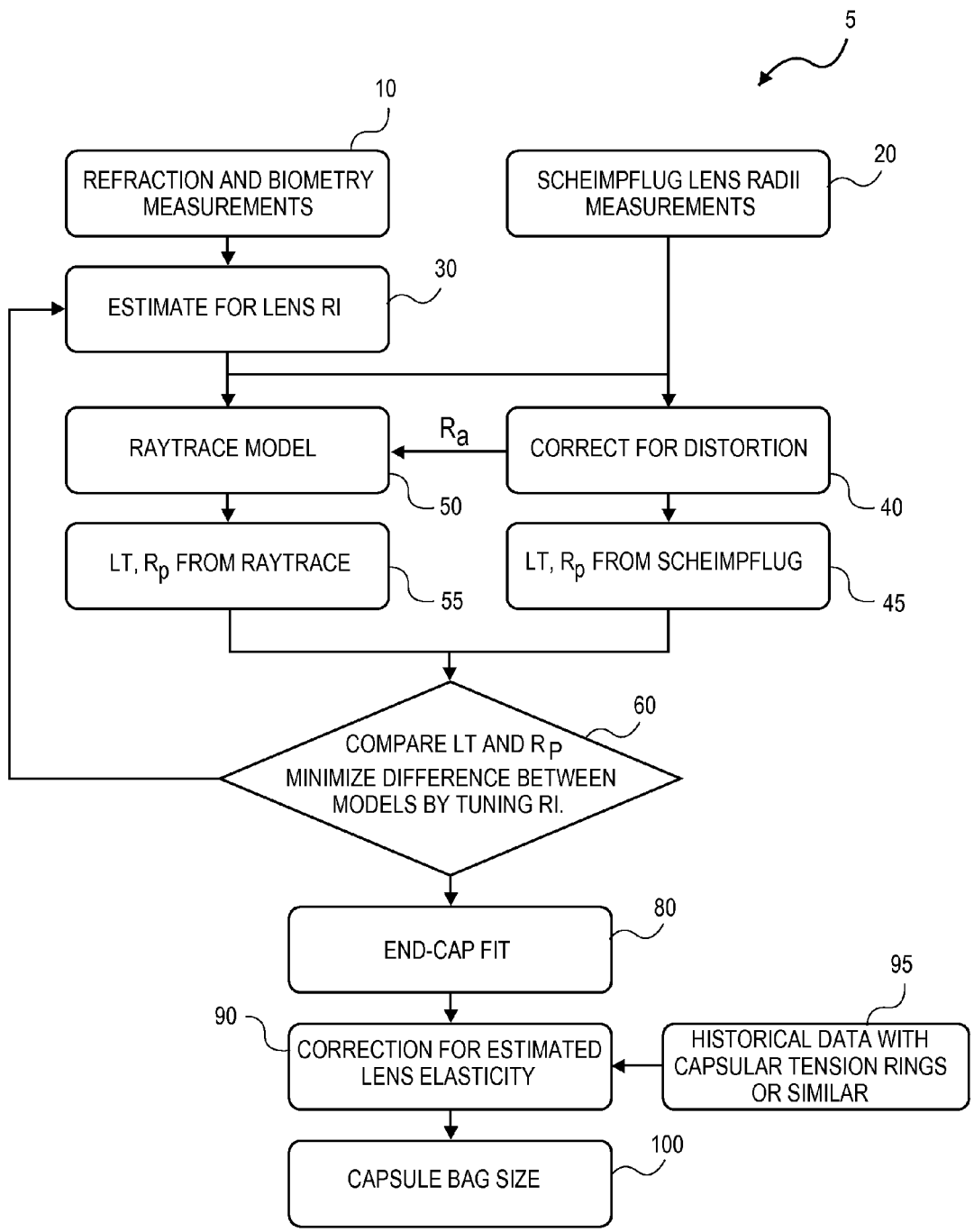
FIG. 1 illustrates an exemplary method of estimating a capsule bag size.

FIG. 1 shows an exemplary embodiment of a method of estimating a capsule bag size. While method 5 comprises a plurality of steps, it is understood that in alternative embodiments of estimating a capsule size not all of the steps included in method 5 need to be included in the estimation of the capsule size. It is also understood that in alternative embodiments the order of the steps in method 5 need not necessarily be adhered to in estimating a capsule size. In some embodiments not only do all of the steps from method 5 not need to be performed, but the order in which they are performed may be different than the order shown in FIG. 1.

Method 5 includes step 10 which comprises obtaining refraction and/or biometry measurements from the subject using, for example without limitation, A-scan, OCT, or other clinical methods. The information obtained in step 10 can include, without limitation, manifest refraction (spectacle correction to achieve emmotropia), corneal power, corneal thickness, keratometry (k-values that can be converted to corneal radius of curvature), axial length, anterior chamber depth, lens thickness, the white-to-white distance, wavefront maps that assist in separating corneal aberrations from lens aberrations or a combination thereof, cataract density, age, gender, and ethnicity. The information obtained in step 10 can be broadly considered patient data.

Method 5 also includes step 20 which comprises obtaining images of the anterior, and if possible, posterior radii of curvature of the native lens using a Scheimpflug imaging system. The accuracy for the measurement of the posterior lens radius of curvature is based on the amount of the lens that can be visualized, a factor of the dilation of the iris.

The Scheimpflug imaging system that may be used to image the anterior and posterior radii of curvature can be, without limitation, the NIDEK EAS-1000 (NIDEK Co. Ltd, Gamagori, Japan), the Topcon SL-45 (Topcon Medical Systems Inc., Paramus, N.J.), the Pentacam (OCULUS Optikgerate GmbH, Wetzlar, Germany), and the GALILEI dual Scheimpflug analyzer (Ziemer Ophthalmology, Port, Switzerland). These and other Scheimpflug imaging systems are described in Dubbelman M, van der Heijde G L, Weeber H A, The thickness of the aging human lens obtained from corrected Scheimpflug images, Optom Vis Sci, 2001; 78:411-416, and Rosales P, Marcos S, Pentacam Scheimpflug quantitative imaging of the native lens and intraocular lens, J Refractive Surgery, 2009; 25: 422-428, the entire disclosures of which, including their references, are incorporated by reference herein.

Method 5 also includes step 30 which comprises estimating the refractive index ("RI") of the lens from any combination of biometry and patient data obtained in step 10 (e.g., cataract density, age, gender, ethnicity, etc.).

Method 5 also includes step 40 which comprises correcting the Scheimpflug images from step 20 for distortion due to imaging through the cornea, anterior chamber, and through the lens. When photographing the anterior and posterior surface of the native lens to measure the anterior and posterior radii of curvature, Scheimpflug imaging systems currently do not account for one or more types of distortion in the imaging process. One type of distortion that is corrected in step 40 is the optical distortion caused by refraction from different ocular surfaces. The radius of curvature of the anterior surface of the lens needs to be corrected for the distortion caused by both the anterior and posterior surfaces of the cornea, while the radius of curvature of the posterior surface of the lens needs to be corrected for the anterior and posterior surfaces of the cornea as well as the anterior surface of the native lens and the refractive index of the native lens (equivalent or gradient refractive index).

The images are corrected to determine the radius of curvature of the anterior surface of the lens ("Ras"), radius of curvature of the posterior surface of the lens ("Rps") and the lens thickness ("LTs"). The subscript "s" is used herein to denote that these measurements are computed from Scheimpflug imaging.

Correcting the Scheimpflug images at step 40 can be accomplished by a raytracing method using estimated refractive indices. For example, methods of correcting for optical distortion are discussed in Dubbleman and Rosales, which are both incorporated by reference herein. For example, Rosales describes correcting the optical distortion by means of raytracing to reconstruct the anterior and posterior surfaces of the lens (see, e.g., FIG. 2 in Rosales). It is noted that the corrective algorithm used may be specific to the particular type of Scheimpflug photography system being used to image the lens (due to the optical path within the instrument), or the corrective algorithm may be able to be applied to more than one particular imaging system.

Figure 2:
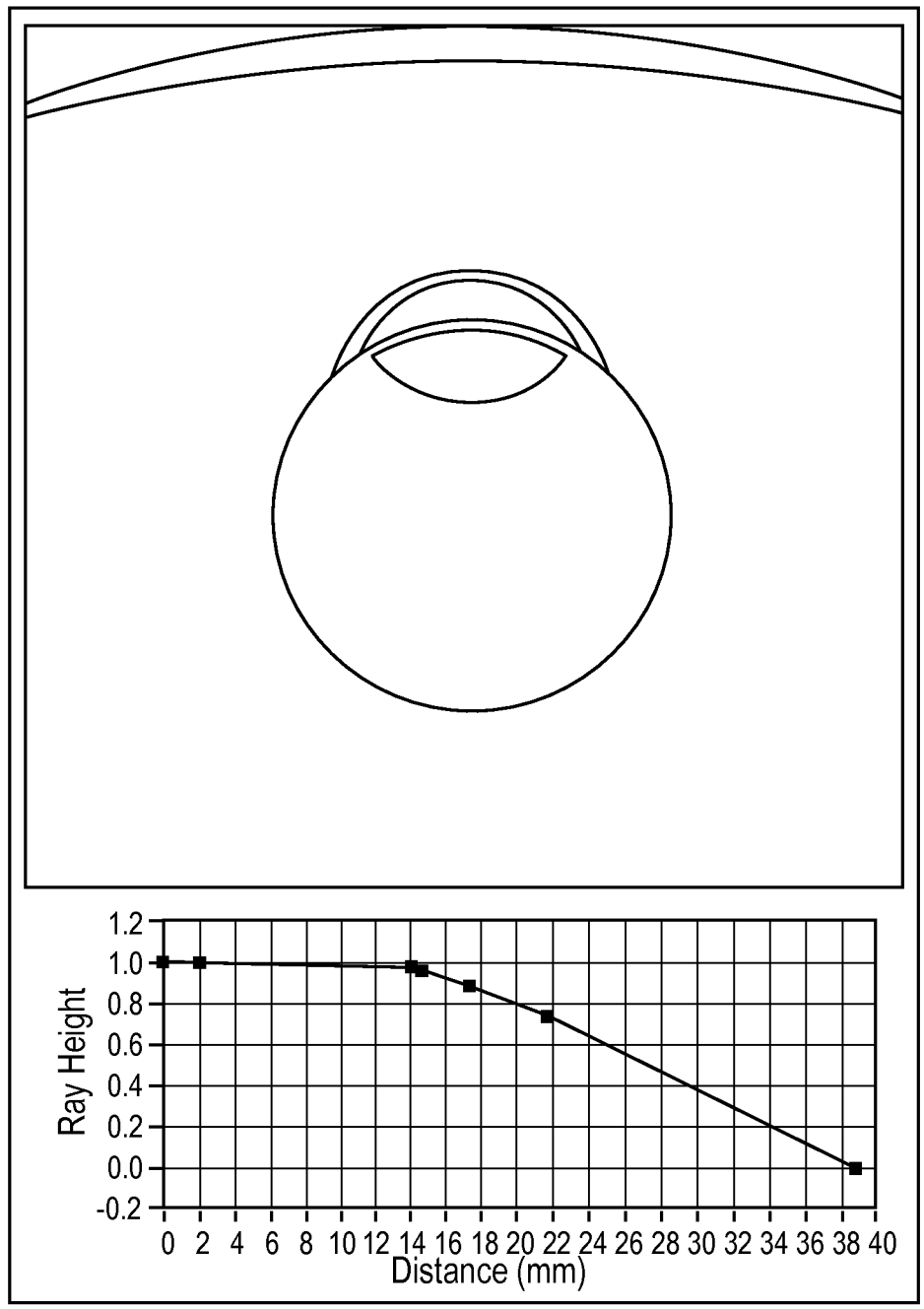
FIG. 2 illustrates performing a raytrace to determine an estimate for the radius of curvature of the posterior surface of the lens using an estimate for the refractive index of the lens, refraction and biometry data, as well as the radius of curvature of the anterior surface of the lens computed from Scheimpflug imaging.

Method 5 also includes step 50 of performing a raytrace (different than the raytrace performed in step 40) to determine at step 55 an estimate for the radius of curvature of the posterior surface of the lens ("Rp") and the lens thickness ("LT") using an estimate for the RI of the lens (from step 30), the subject's refraction and biometry data, as well as Ras. FIG. 2 illustrates an exemplary model for performing a raytrace from step 50. FIG. 2 shows the radii that define the spectacles (glasses), the cornea, the crystalline lens, and the retina. The y-axis in the graph in FIG. 2 is the ray height from a paraxial raytrace and if the model parameters are adjusted correctly the ray height should be zero at the final point corresponding to the retina to ensure that the image is in-focus.

Method 5 also includes step 60 which comprises comparing the resultant lens thicknesses and radii of curvature of the posterior surface of the lens from the two models (i.e., comparing the results from step 45 and step 55). Step 60 further includes minimizing the difference between one or more of the measurements by repeating the modeling while iteratively changing the refractive index.

Figure 3:
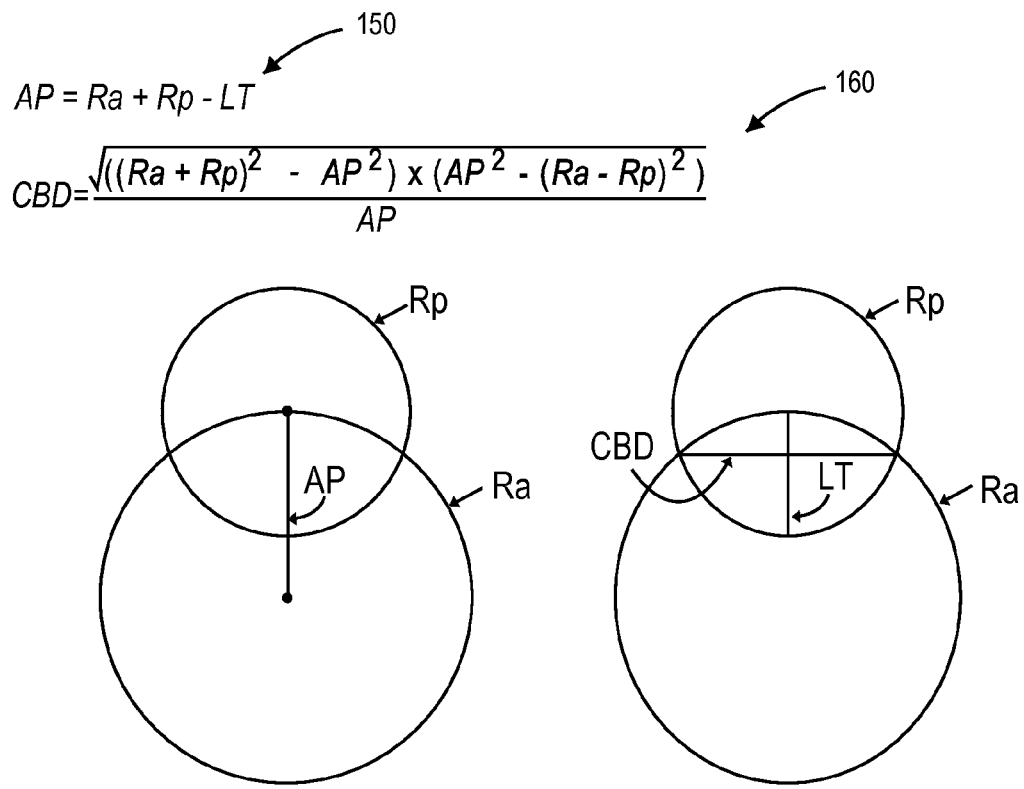
FIG. 3 illustrates a geometric model for computing the capsular bag diameter.

Once satisfactory agreement between the models is found after iteratively modifying the refractive index, step 70 (not shown in FIG. 1, but which, in method 5, follows step 60 and occurs before step 80) is performed, which fits the anterior radius, posterior radius, and lens thickness to a simple geometric model to compute the capsule bag diameter ("CBD"). FIG. 3 illustrates the method of computing the CBD. This is done by assuming the centers of the circles with radii Rp and Ra are aligned on-axis, as is shown in FIG. 3. The distance between the centers, AP, is calculated using equation 150, and the distance between the intersections of the circles (CBD) is calculated using equation 160.

Figure 4:
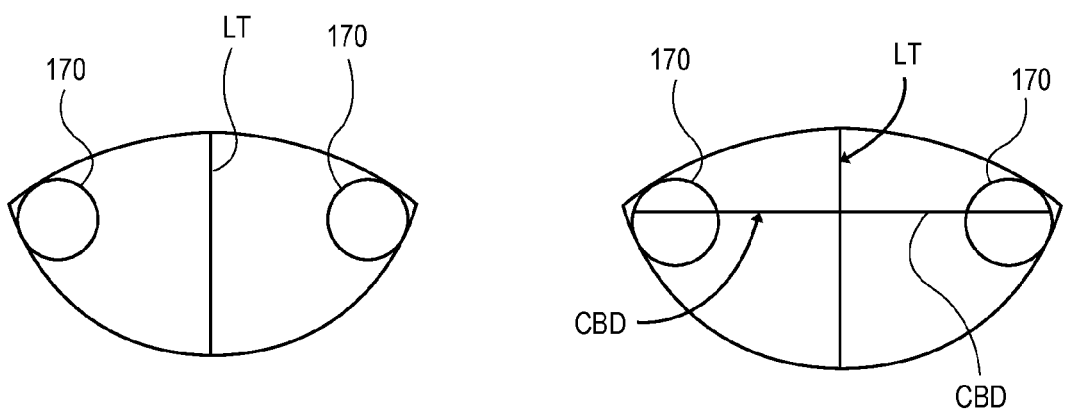
FIG. 4 describes an optional end-cap fitting to refine the capsular bag diameter measurement.

Method 5 also includes optional step 80 of fitting end-caps 170 (see FIG. 4) to further refine the CBD measurement. The end caps are mathematically calculated by adjusting the lens anterior and posterior surfaces so that the first derivatives are zero at the lens equator and both surfaces meet at this location. It is a polynomial approximation with fraction exponents that become the dominant terms as the surfaces extend to the lens equator.

Once the capsule geometry is reconstructed through the described method using end caps, the capsular bag volume or any other measurement related to the capsule geometry can be determined.

Method 10 also includes optional step 90 which comprises correcting for estimated lens elasticity. If enough capsular tension ring or similar data has been collected (step 95), this correction may be applied to account for the elasticity of the capsule by comparing the data from step 95 with the prior CBD result.

Once the capsule size is estimated at step 100, an appropriately sized IOL can be selected, from a kit of IOLs, to be implanted based on the capsule size estimation. For example, if the volume of the capsule has been estimated during the method, the IOL to be implanted can be selected at least in part based on the estimated volume of the capsule. Alternatively, the capsule size estimation method may be used to manufacture or design a patient-specific IOL.

Exemplary IOLs which can be implanted in the capsule based on the capsule size estimation methods include those, without limitation, described in U.S. Pat. No. 7,122,053, U.S. Pat. No. 7,261,737, U.S. Pat. No. 7,247,168, U.S. Pat. No. 7,217,288, U.S. Pat. No. 6,935,743, U.S. Patent Application Publication 2007/0203578, U.S. Patent Application Publication 2007/0106377, U.S. Patent Application Publication 2005/0149183, U.S. Patent Application Publication 2007/0088433, U.S. Patent Application Publication, and U.S. Patent Application Publication 2008/0306588, all of which are incorporated by reference herein.

The current disclosure is also related to Provisional Patent Application No. 61/143,559, filed Jan. 9, 2009, entitled Lenses and Methods of Accounting for Different Lens Capsule Sizes and Changes to a Lens Capsule Post-Implantation, which is incorporated by reference herein.

One or more of the steps in the methods described herein can be performed by instructions on any computer-readable medium for use by or in connection with an instruction execution system, apparatus or device, such as a computer-based system, processor-containing system, or any system that can fetch the instructions from the instructions execution system, apparatus, or device and execute the instructions. A "computer-readable medium" as used herein can be any medium that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM) (magnetic), an optical fiber (optical), portable optical disc such a CD, CD-R, CD-RW, DVD, DVD-R, or DVD-RW, or flash memory such as compact flash cards, secured digital cards, USB memory devices, memory stick, etc. Note that the computer-readable medium could even be paper or another suitable medium upon which the program is printed, as the program text can be electronically captured via optical scanning of the paper or other medium, then compiled, interpreted or otherwise processed in a suitable manner if necessary, and then stored in a computer memory.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method of estimating the size of an ocular lens capsule, comprising:
   obtaining patient data of a subject;
   imaging an anterior surface of an ocular lens and a posterior surface of the ocular lens;
   estimating a refractive index of the ocular lens;
   correcting the image of the anterior surface of the ocular lens for distortion to determine a radius of curvature of the anterior surface of the ocular lens;
   correcting the image of the posterior surface of the ocular lens for distortion to determine a radius of curvature of the posterior surface of the ocular lens;
   determining a thickness of the ocular lens using the corrected images of the anterior and posterior surfaces;

estimating an estimated radius of curvature of the posterior surface of the ocular lens and an estimated lens thickness using the estimated refractive index, the patient data, and the radius of curvature of the anterior surface of the ocular lens;

determining a difference between the determined radius of curvature of the posterior surface and the estimated radius of curvature of the posterior surface, and determining a difference between the thickness of the lens and the estimated lens thickness;

minimizing at least one of the differences by repeating the estimating step and the determining step with an adjusted estimated refractive index;

creating a geometric model of the capsule using the radii of curvature of the anterior surface, the posterior surface, and the lens thickness, using a processor; and selecting an intraocular lens for implantation based on the computed geometric model.

2. The method of claim 1 further comprising computing a capsular bag diameter from the geometric model.

3. The method of claim 1 wherein estimating the refractive index comprises estimating a refractive index of the ocular lens using the patient data.

4. The method of claim 1 wherein the method further comprises fitting end caps into the geometric model to compute the capsular bag diameter.

5. The method of claim 1 wherein the method further comprises using an estimated lens elasticity to compute the capsular bag diameter.

6. The method of claim 1 wherein imaging an anterior surface of an ocular lens and a posterior surface of the lens comprises imaging the anterior surface of an ocular lens and a posterior surface of the lens with a Scheimpflug imaging system.

* * * * *